United States Patent
Cormier et al.

(10) Patent No.: US 7,037,287 B2
(45) Date of Patent: May 2, 2006

(54) ADJUSTABLE ERGONOMIC KNEE BRACE

(75) Inventors: David Cormier, Oxnard, CA (US); Tracy E. Grim, Bixby, OK (US); Joseph M. Iglesias, Newbury Park, CA (US); Hugo A. Cobar, Tarzana, CA (US); Janelle R. Batman, Pasadena, CA (US)

(73) Assignee: Royce Medical Company, Camarillo, CA (US)

( * ) Notice: Subject to any disclaimer, the term of this patent is extended or adjusted under 35 U.S.C. 154(b) by 147 days.

(21) Appl. No.: 10/675,324

(22) Filed: Sep. 29, 2003

(65) Prior Publication Data

US 2005/0070831 A1 Mar. 31, 2005

(51) Int. Cl.
*A61F 5/00* (2006.01)

(52) U.S. Cl. ............................... 602/23; 602/16; 602/26
(58) Field of Classification Search ................... 602/16, 602/26, 3, 20–23, 28–29; 128/80 C, 878, 128/881, 8 R, 8 C, 8 F, 8 H, 77; 473/59; 623/31, 40–46, 60; 403/92–93, 95
See application file for complete search history.

(56) References Cited

U.S. PATENT DOCUMENTS

| | | | | |
|---|---|---|---|---|
| 2,632,440 A | * | 3/1953 | Hauser et al. ................ 602/16 |
| 4,520,804 A | * | 6/1985 | DiGeorge ..................... 602/16 |
| 4,576,151 A | * | 3/1986 | Carmichael et al. .......... 602/24 |
| 4,620,532 A | * | 11/1986 | Houswerth .................... 602/16 |
| 4,817,588 A | * | 4/1989 | Bledsoe ........................ 602/16 |
| 4,886,054 A | | 12/1989 | Castillo et al. |
| 4,982,732 A | | 1/1991 | Morris |
| 5,000,169 A | | 3/1991 | Swicegood et al. |
| 5,135,469 A | | 8/1992 | Castillo |
| 5,409,449 A | | 4/1995 | Nebolon |
| 5,421,810 A | * | 6/1995 | Davis et al. ................... 602/16 |
| 5,460,599 A | | 10/1995 | Davis et al. |
| 5,571,078 A | * | 11/1996 | Malewicz ..................... 602/27 |
| 5,611,773 A | | 3/1997 | Nash et al. |
| 5,740,054 A | * | 4/1998 | Durr et al. .................... 700/122 |
| 5,814,000 A | * | 9/1998 | Kilbey ......................... 602/16 |
| 5,827,208 A | | 10/1998 | Mason et al. |
| 5,873,847 A | * | 2/1999 | Bennett et al. ............... 602/16 |
| 5,997,493 A | | 12/1999 | Young |
| 6,045,524 A | * | 4/2000 | Hayashi et al. ............... 602/23 |
| 6,656,144 B1 | * | 12/2003 | Coligado ...................... 602/16 |

FOREIGN PATENT DOCUMENTS

| | | |
|---|---|---|
| EP | 1 475 060 A1 | 11/2004 |
| WO | WO 02/02035 A | 1/2002 |

OTHER PUBLICATIONS www.innovationsports.com website, SENTRY and KNEE M.D. post–op knee brace, 5 pp. (1999).

* cited by examiner

*Primary Examiner*—Henry Bennett
*Assistant Examiner*—Shumaya B. Ali
(74) *Attorney, Agent, or Firm*—Fulwider Patton Lee & Utecht, LLP

(57) ABSTRACT

A knee brace is provided with push button actuatable stops, wherein the stops are biased outward into angular locking positions and inwardly directed pressure on the push buttons releases the stops and permits angular adjustment of the stops. A pair of catch plates with locking recesses facing inward, are provided, and outwardly biased locking pins engage the recesses in both catch plates. Each of the stop assemblies has an outwardly directed plate extending over the outer cover plate, and this plate is coupled to the physical stop member around the outer edge of the outer cover plate. The cover plate has angular indicia thereon, which may be viewed through windows in the outwardly extending plate portions of the stop assemblies.

19 Claims, 7 Drawing Sheets

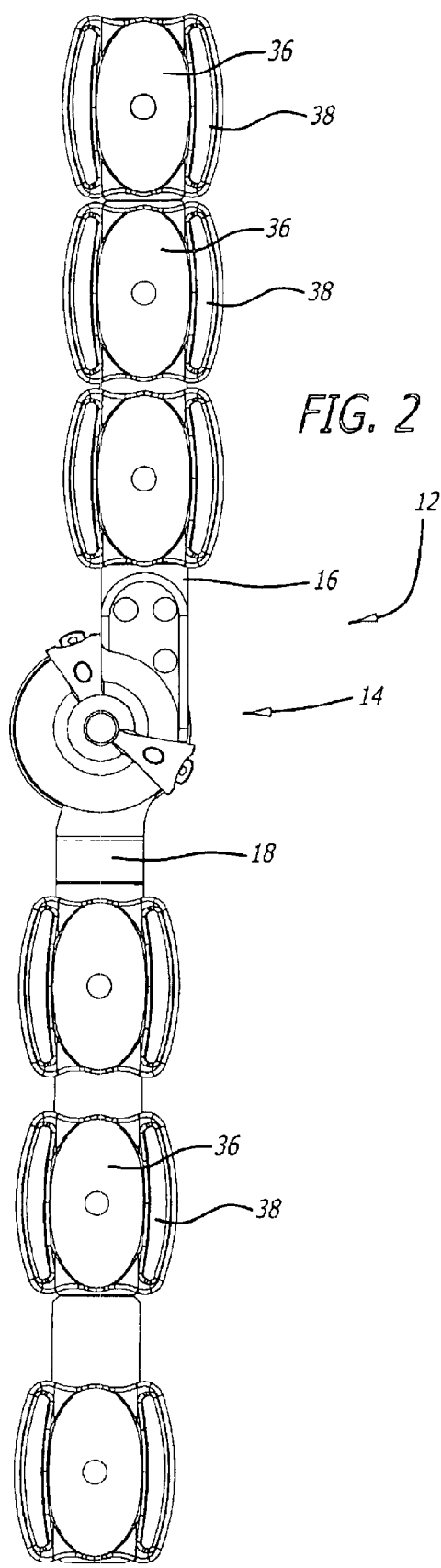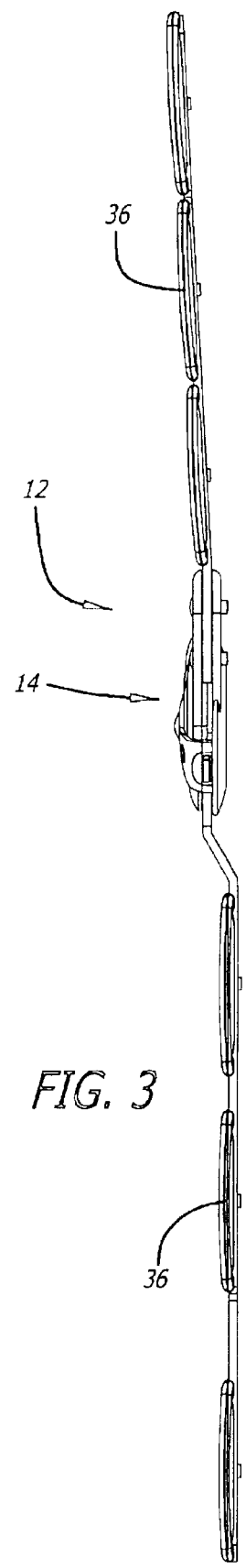

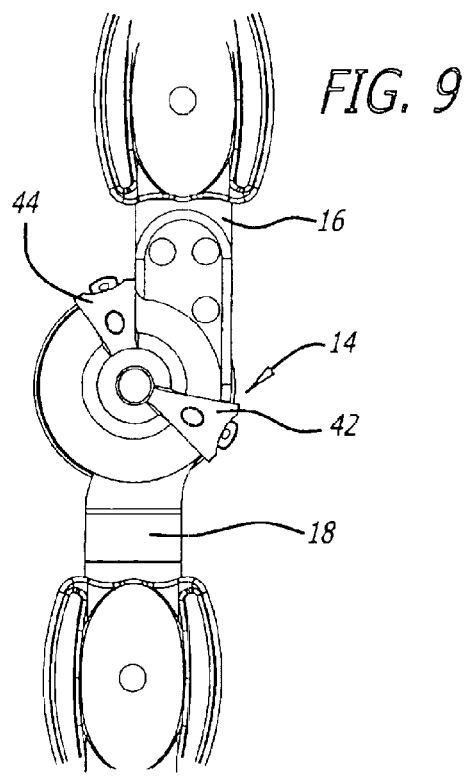
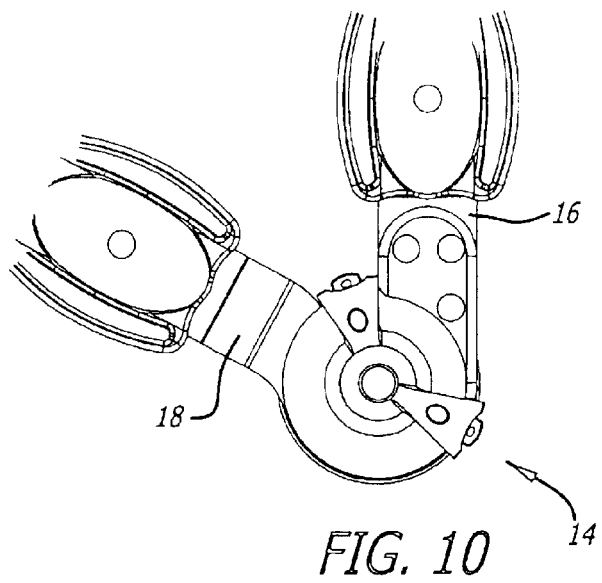
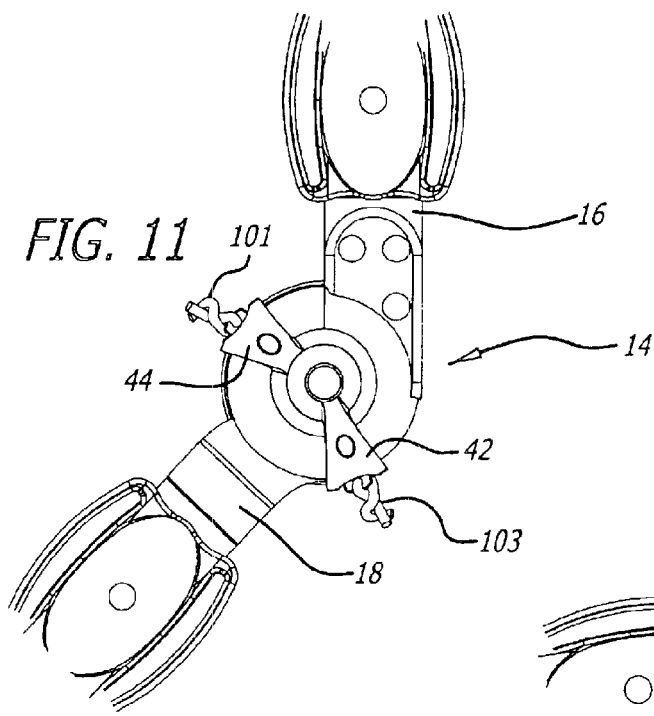
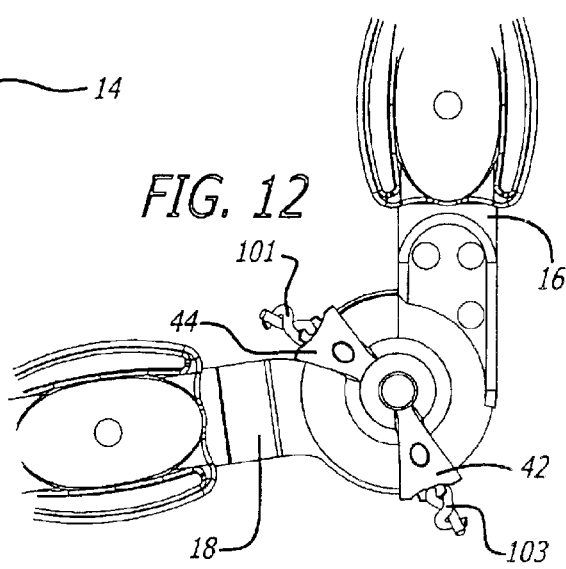

ADJUSTABLE ERGONOMIC KNEE BRACE

FIELD OF THE INVENTION

This invention relates to ergonomic knee braces.

BACKGROUND OF THE INVENTION

In the field of adjustable knee braces or supports, it is desirable that the brace include arrangements for limiting the movement of the lower leg relative to the upper leg both as to bending the knee or flexion, and as to extension of the lower leg relative to the upper leg. Various knee brace arrangements have been proposed, and these have included upper struts for extending along the thigh, and lower struts for extending along the lower leg or calf. These are normally provided both on the inside or medial side of the leg and also on the outer or lateral side of the leg; and the medial and lateral struts are normally padded, and provided with straps to hold them in place. Pivoting arrangements are provided for coupling the upper and lower struts, and stops are provided for limiting both extension and flexion of the knee.

The prior art patents in the field of knee braces include U.S. Pat. No. 5,672,152 granted Sep. 30, 1997; U.S. Pat. No. 5,921,946, granted Jul. 13, 1999; U.S. Pat. No. 4,817,588, granted Apr. 14, 1989, U.S. Pat. No. 4,953,543 granted Sep. 4, 1990, and U.S. Pat. No. 4,620,532 granted Nov. 4, 1986. Although many of the foregoing provided useful results, these prior art knee braces had shortcomings, in that they were unduly bulky, or were not simple to adjust, or did not have as many stop increments as would be desired, or were otherwise not ergonomically configured.

INVENTION SUMMARY

Accordingly, objects of the invention include providing a knee brace which is compact, easy to use, which has many points of adjustment and is otherwise ergonomically configured. Preferably the adjustments should be simple and natural so that there is no need to resort to collateral written instructions.

Initially, relative to an illustrative preferred embodiment of the present knee brace, the knee brace stop construction operates at the periphery of the pivot arrangements so that the number of stop increments is maximized for the size of the pivot discs. Secondly, the stops may be operated by simple inward pressure on a push button associated with the flexion stop or the extension stop, to release the stop, followed by rotation of the stop to virtually any desired angle, and then followed by release of the push button to permit locking of the stop in the new angular position. With this simplified ergonomic construction, the stop adjustments may be easily made while the brace is mounted on the leg; and the mode of accomplishing stop adjustments is substantially self evident, with the shifting of the stops resulting in the natural or expected angular change in flexion or extension stops.

In order to achieve the foregoing results in one illustrative embodiment, the pivoting assembly interconnecting the upper and lower struts includes, for both extension and flexion, at least one generally circular or arcuate catch plate with stop recesses facing or opening inward toward the center of the assembly, and a movable stop member pivoted at the center of the assembly and having an outwardly biased locking member for selectively engaging one of the stop recesses, and with the locking member attached to a release button which extends radially outward to the periphery of the pivot assembly.

Viewed from a different aspect, the pivoting assembly may include an outer cover or closure plate and an inner cover or closure plate; an arcuately configured array of locking steps; a movable stop member pivoted at the center of the assembly and having an outwardly biased locking member for selectively engaging at least one of the locking steps; and with the locking member attached to a release button which is located radially outward at the periphery of the pivot assembly.

Additional features may include the provision of angular indicia on the outer surface of the outer one of said cover or closure plates and the implementation of the movable stop assembly by an outer, radially extending flat support member adjacent the indicia, preferably with a window through which the angular indicia may be seen. Further, the movable stop assembly may extend over the edge of one of said plates into the space between the two cover plates to cooperate with the locking steps. This construction contributes to the relatively thin overall configuration of the pivoting assembly, which may be only about one-half inch or about 1.3 cm thick. Also, to provide adequate strength and compactness, the brace and it components are preferably made of high strength material such as steel, titanium, zinc alloys, or other high strength metals or high strength plastic.

It is further noted that, in the preferred design, two catch plates are provided, and each of the stop assemblies includes a pin which seats in corresponding recesses in each of the two catch plates, to provide a balanced locking configuration for resisting forces applied between the struts to limit flexion or extension. The inner and outer cover plates may also have complementary recesses to more positively secure the stops at the selected angular position.

Referring back to the overall construction as mentioned above, one strut extends from the knee pivot assembly up the upper leg or thigh, and the other strut extends from the pivot assembly down the lower leg. The pivot stop assembly is mounted on the end of a first one of these struts, and the second strut has stop surfaces on its end adjacent the stop assembly which engage the flexion and extension stops. Further, the catch plates as described above are mounted on opposite sides of this second strut, with the locking member of the movable stop assembly engaging locking steps on both of the two catch plates, so that a balanced positive stopping force is transmitted to the second strut when the stop surfaces on the end of the second strut engage the flexion stop or the extension stop.

Additional aspects of the knee brace may include the following:

(1) catch plates which have separate sets of notches for the flexion and extension stops, and a mechanical coupling between these two sets of notches;

(2) Color coded flexion and extension actuation buttons, with the degree indicia set forth in matching different colors;

(3) Apertures or holes in the actuation buttons to permit locking of the buttons against change.

Other objects, features and advantages of the invention will become apparent from a consideration of the drawings and from the detailed description.

BRIEF DESCRIPTION OF THE DRAWINGS

FIG. 2 is a plan view of one of the two knee braces included in the knee brace assembly of FIG. 1;

FIG. 3 is a side view of the knee brace of FIG. 2;

FIG. 9 through 12 show various stop adjustment configurations for the knee brace.

DETAILED DESCRIPTION OF THE PREFERRED EMBODIMENTS

While the specification describes particular embodiments of the present invention, those of ordinary skill can devise variations of the present invention without departing from the inventive concept.

Figure 1:
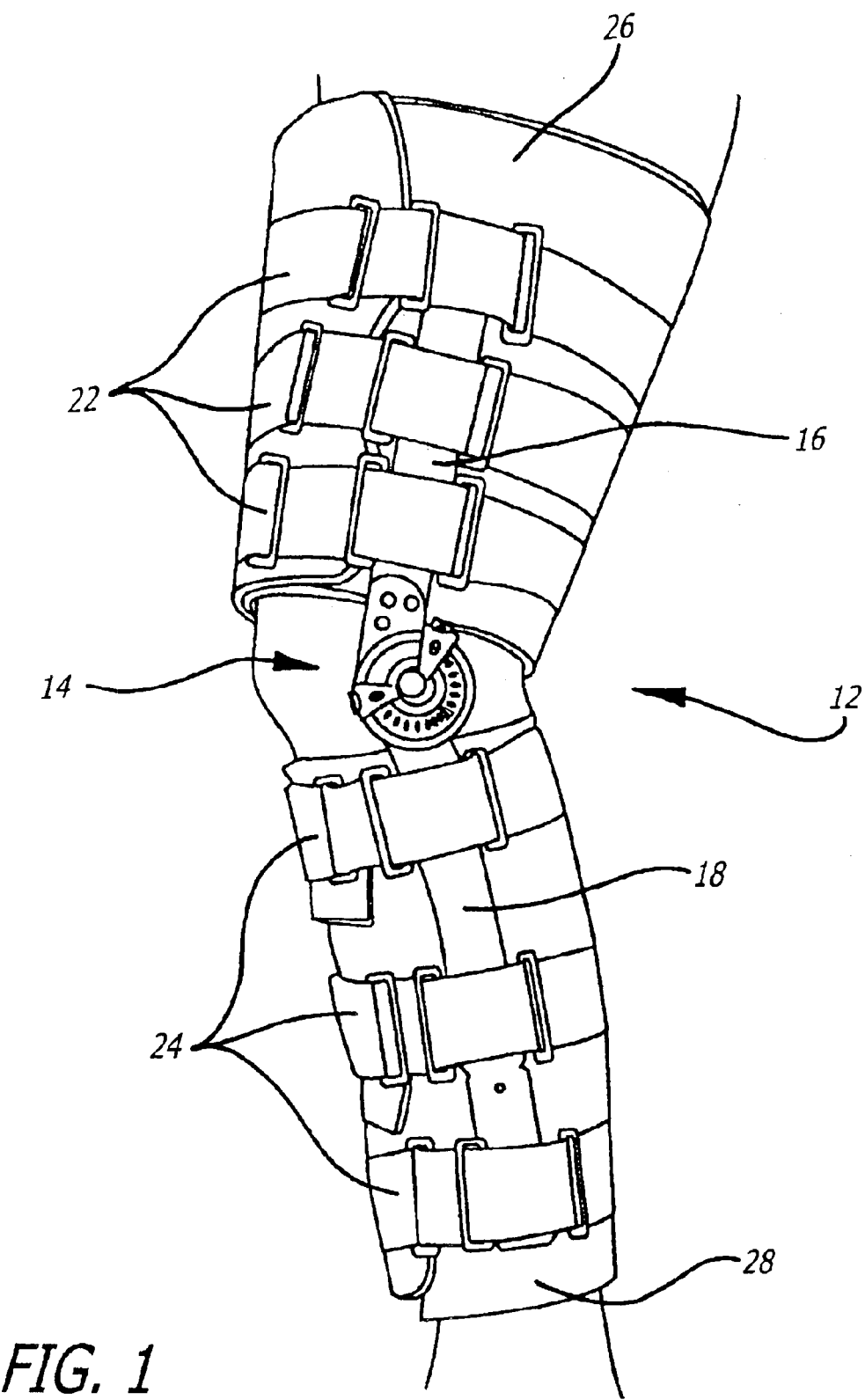
FIG. 1 is a perspective view of a knee brace assembly illustrating the principles of the invention.

Referring more particularly to the drawings, FIG. 1 shows a leg brace 12 for the knee, including two struts extending up and down the leg from a central pivot assembly 14. Extending along the upper leg is a strut 16, and extending down the lower leg from the pivot assembly 14 is a lower strut 18. These struts are sometimes referenced as femoral struts (as extending along the femur or upper leg bone) and tibial struts (extending along the tibia, or the principal lower leg bone). A pivot assembly on the other side of the knee is also provided with struts extending up and down the leg, but these are not visible in FIG. 1.

To hold the struts in place on the leg are a series of straps 22 on the upper leg, and straps 24 on the lower leg. Suitable padding 26 is provided on the upper leg and the struts are normally secured to the padding 26 by appropriate Velcro® or hook and loop type material. Similar padding 28 underlies the strut 18 and straps 24. The straps 22 extend through the loops 38 to hold the entire assembly together under active usage conditions.

The present invention is directed primarily to the pivot stop assemblies which interconnect the struts. For a postoperative patient, it is desirable to be able to limit the bending of the knee both in the extension direction when the patient is straightening his or her leg, and in the flexion direction where the patient is bending the leg at the knee as far as practical under the circumstances.

The showing of FIG. 1 is of the outside of the left leg. On the inside of the left leg is a similar assembly, to that shown in FIG. 1, with two struts and a central pivot assembly. The two units are similar and both are held to the leg by the straps 22 and 24. Most of the parts are common to the inner and outer assemblies, but with the struts and the cover plates being mirror images of one another.

Figure 6:
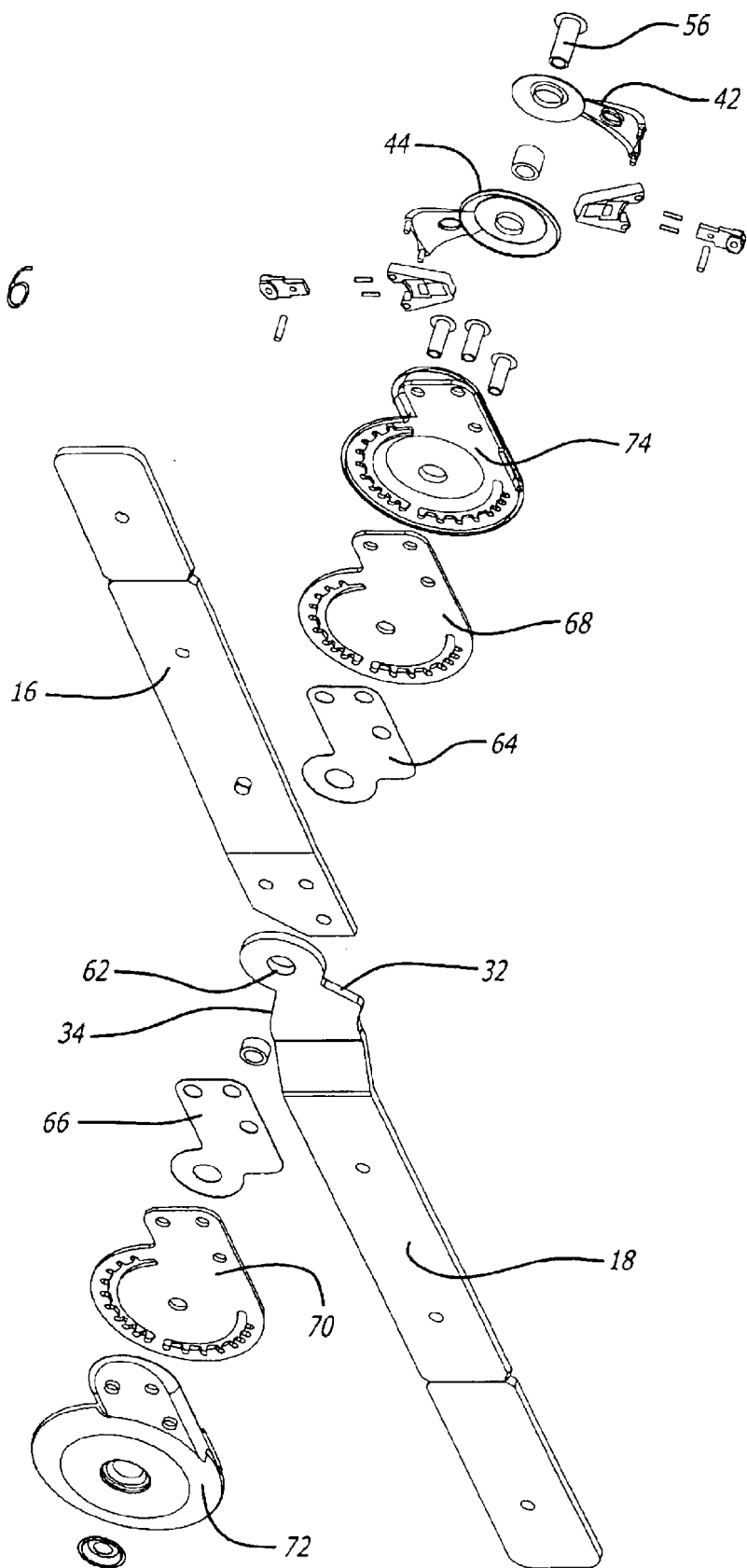
FIG. 6 is an exploded view of the knee brace assembly illustrating the principles of the invention.

To better understand the operation of the entire assembly, it is useful to refer briefly to the exploded view of FIG. 6. In operation, the two struts 16 and 18 are pivoted relative to one another about center rivet 56; and strut 18 has two stop surfaces 32 and 34. Adjustable stops are mounted to the hinge pivot assembly 14 on strut 16 and the adjustable stops engage stop surfaces 32 and 34 to limit pivoting of the knee in both the extension and the flexion directions.

FIG. 2 of the drawings shows the assembly 12 and the pivot assembly 14 with the straps 22 and 24, and the padding 26 and 28 removed. Visible in FIG. 2 are the strap coupling members 36 which are secured to the struts, and the strap receiving openings 38. FIG. 3 is a side view of the assembly of FIG. 2. The central stop mechanism 14 will be described in greater detail hereinbelow.

Figure 4:
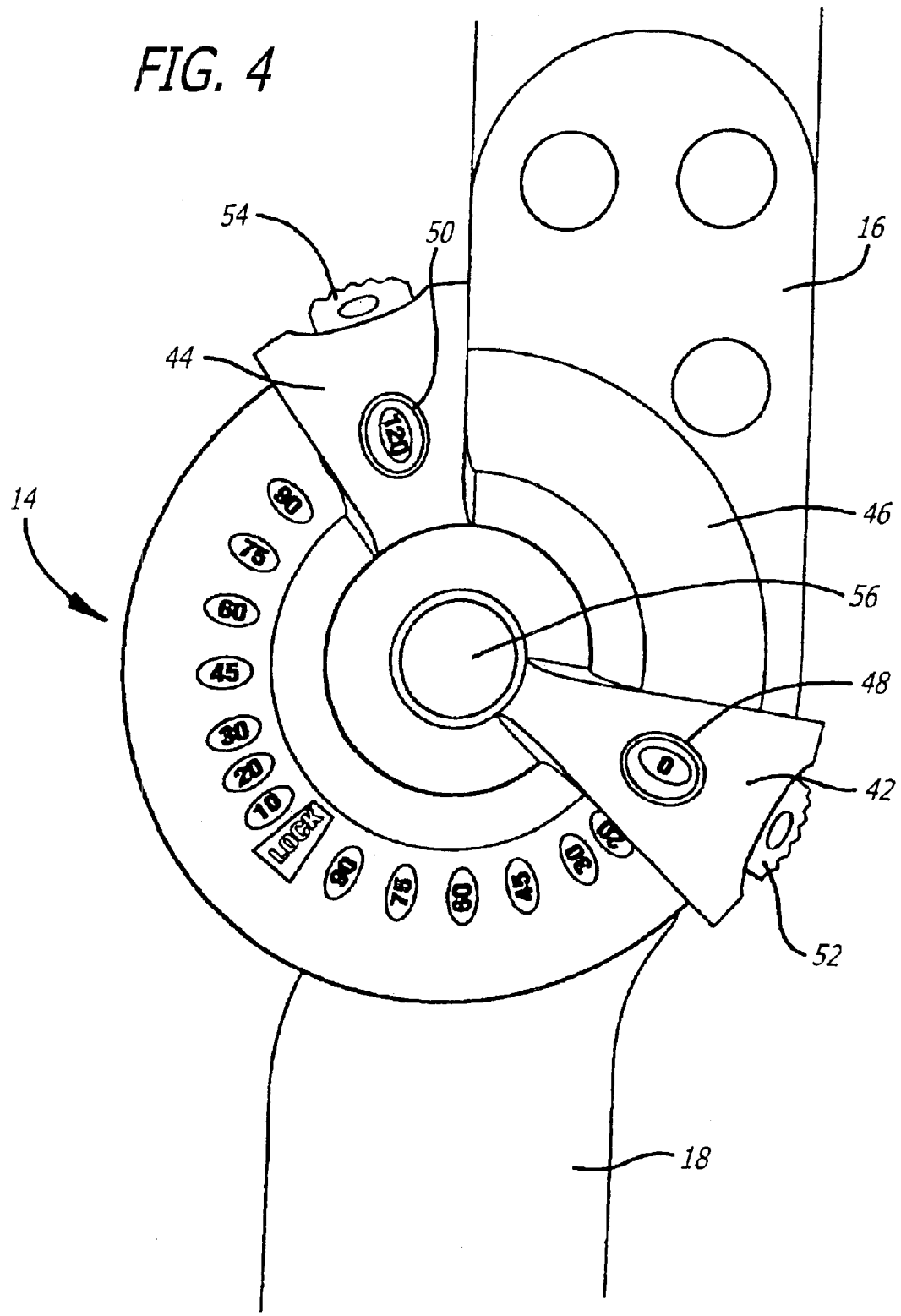
FIG. 4 is an enlarged plan view of a knee brace pivot and motion limiting assembly, illustrating the principles of the invention.
Figure 5:
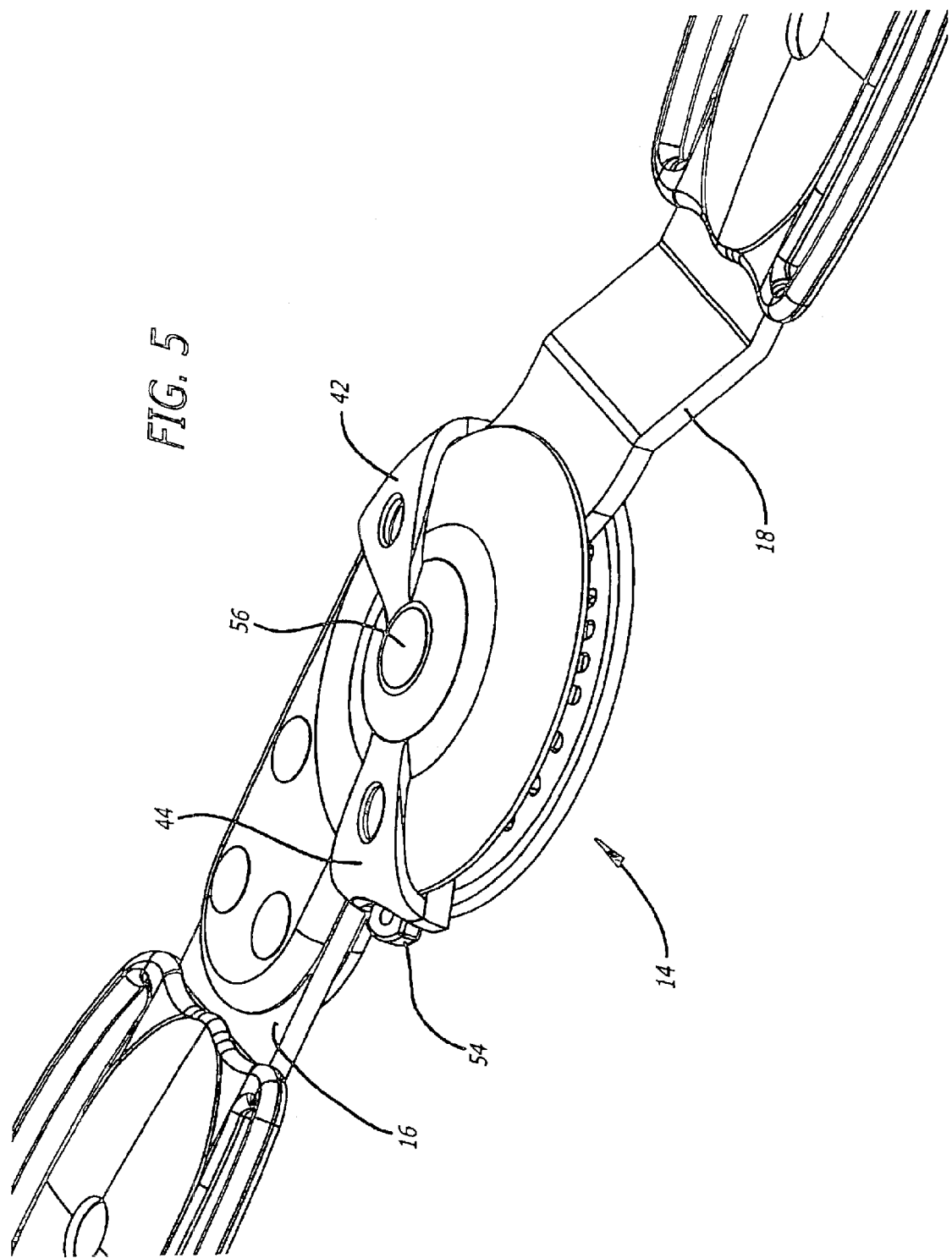
FIG. 5 is an enlarged perspective view of the pivot assembly.

Referring now to FIGS. 4 and 5 of the drawings, these are plan and perspective views, respectively of the central stop mechanism 14 which interconnects the struts 16 and 18.

Now, considering FIG. 4 in detail, it includes the extension stop assembly 42 and the flexion stop assembly 44. Visible on the cover plate 46 are degree indicia which may be read through the openings 48 and 50 on the stop assemblies 42 and 44, respectively. To change the limits of motion, the push buttons 52 and 54 are depressed and the stop assemblies are rotated to the desired angular settings. Incidentally, the outermost surfaces of push buttons 52 and 54 are preferably knurled, ribbed or textured for non-slip engagement. Alternatively the stops may be coated with a frictional coating.

Concerning the angular settings, when the extension stop 42 is at zero degrees (0°), the patient is free to fully extend his lower leg. When the extension stop 42 is set to 90°, the lower leg is restrained from movement beyond 90° relative to the upper leg, so the lower leg cannot be straightened out.

Regarding the flexion stop 44, when it is set to 120° the lower leg may be fully bent toward the upper leg. When the flexion stop is set to "lock", then the lower leg is fully extended, and is blocked from any bending. If both stops 42 and 44 are set to 60° for example, the knee is held at 60° from fully open, and is restrained from movement in either direction.

Incidentally, the support members for the stops are both pivoted about the center 56 of the pivot assembly 14, with the reference number 56 representing the head of a rivet extending through the assembly.

Consideration will now be given to the detailed construction of the pivotal stop mechanism, by reference to the exploded view of FIG. 6. As mentioned above, one of the two struts 18 has the two stop surfaces 32 and 34 on its end, and is pivoted, with opening 62 receiving rivet 56 which extends through the entire assembly. The flat parts 64 and 66 are spacers and also serve the function of washers in facilitating rotation of the overlying parts. They may be formed of plastic such as nylon. The catch plates 68 and 70 have a series of inwardly opening recesses which receive outwardly biased locking pins as described below.

The inner cover plate 72 and the outer cover plate 74 may also be provided with inwardly directed recesses, matching those in the catch plates 68 and 70. This provides supplemental restraint for the locking pins shown in detail in later figures of the drawings.

Figure 7:
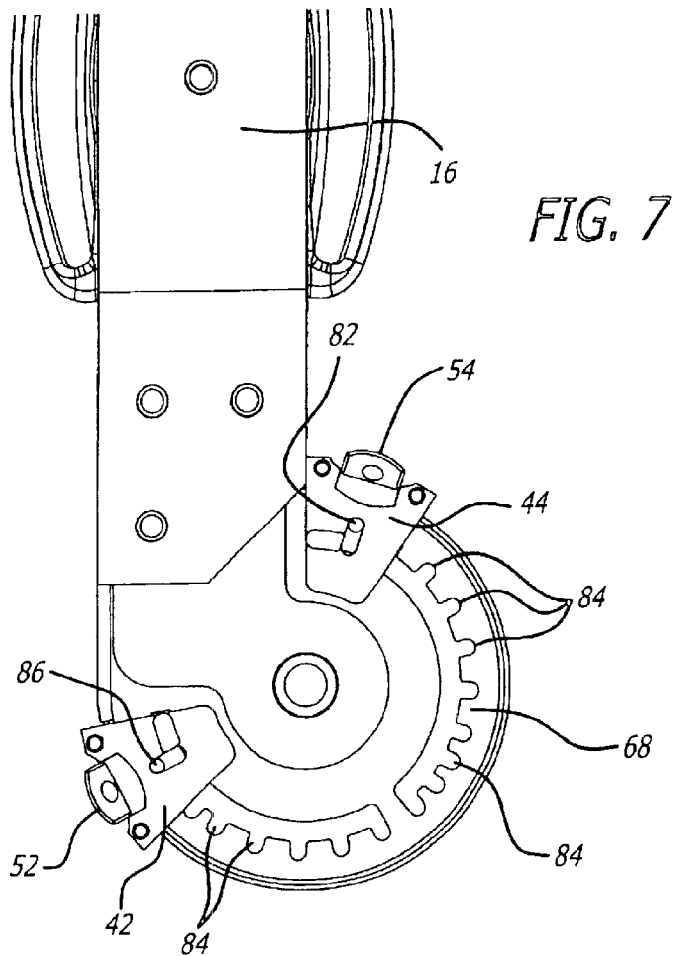
FIG. 7 is an enlarged view of the central pivot and stop assembly of the knee brace of FIGS. 1–6, with the front cover removed.

FIG. 7 is an enlarged view of the central mechanism with one of the cover plates removed. The stop assembly 44 has a locking pin 82 which moves inward with the push button 54 to change settings, but is spring biased outward to engage one of the recesses 84. Similarly, the locking pin 86 associated with push button 52, locks the stop 42 by engagement with a selected one of the catch plate recesses 84.

Figure 8:
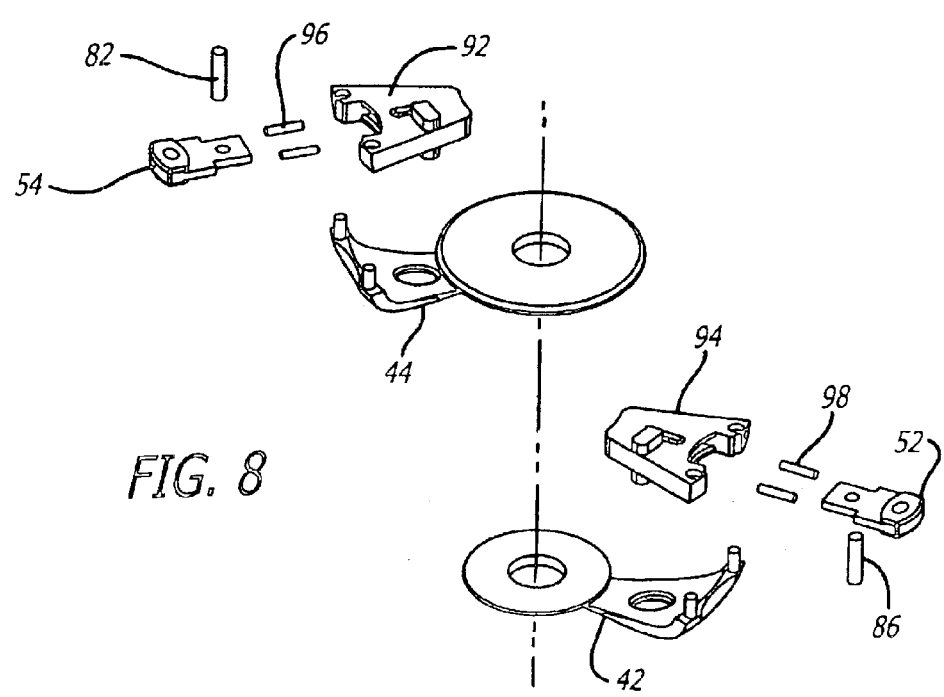
FIG. 8 is an exploded view of the two movable stops and their associated adjustment buttons, and indication support members.

FIG. 8 is an enlarged showing of the physical stop members 92 and 94 which engage the stop surfaces 32 and 34 as shown in FIG. 6. Two small pairs of coil springs 96 and 98 serve to bias the push buttons 52 and 54, and the associated locking pins 86 and 82 outward, into engagement with the catch plate 68 (see FIG. 7) and the other catch plate 70 (see FIG. 6).

Incidentally, the physical stops 92 and 94 may be formed of a high strength zinc alloy referenced as ZA-28, or other high strength material.

FIGS. 9 through 12 shows various adjustments of the stops, and the resultant permitted positions of the struts 16 and 18. More specifically, FIG. 9 shows the extension stop 42 and the flexion stop 44 in their positions for full range of motion, with the extension stop 42 at 0° and the extension stop 44 at 120° (see FIG. 4). In FIG. 9 the struts (and the leg) are fully extended; while in FIG. 10, the struts and the leg are bent to their extreme flexed position, with the two stops in the same positions for both FIG. 9 and FIG. 10.

FIG. 11 is a similar pair of drawings with the extension stop at about 45° and the flexion stop at about 75° in both figures. In FIG. 11 the struts are extended as far as possible with this setting of stops 42 and 44; and in FIG. 12 the struts (and leg) are bent as far as permitted with this setting of the stops 42 and 44.

An alternative embodiment of the stop mechanism may include a physical stop having a radially extending slot for receiving a locking pin associated with a push button; and a wire spring biasing the push button and locking pin radially outward relative to the stop support members.

Concerning another matter, with reference to FIG. 4 of the drawings, the push buttons 52 and their associated assemblies are preferably color coded to match colored angle indicia. Thus, push button 52 may be colored blue, with the associated degree indicia from "0" to "90" degrees being the same blue color; and push button 54 and associated indicia may be colored green.

It may be noted that the push buttons are provided with holes near the outer ends thereof. This permits the physician or technical assistant to thread wire or plastic ties through the openings to discourage re-setting or tampering with the angular settings, as shown at reference numerals 101 and 103 in FIGS. 11 and 12 of the drawings. Other elements for preventing or restricting actuation of the push buttons, including locking ties, may be employed; and these elements may be separate from or integral with and movable with respect to, the knee brace assembly.

It is to be understood that the foregoing detailed description discloses one preferred illustrative embodiment of the invention. Various changes and modifications may be made without departing from the spirit and scope of the invention. Thus, by way of example and not of limitation, instead of having catch plates with locking recesses, a series of outwardly extending rods or protrusions may be provided, with the stop buttons having an outwardly biased fork member for engaging the rods and thereby positioning the stop body or stop plate in the desired angular position. In addition, while the disclosed configuration of the stop supports 44 and 48 is preferred, the stop assemblies may be pivotally mounted within the cover plates as well as, or instead of, extending over the outer surface of the outer cover plate. With regard to another matter, the release push button may be integral with the physical stops. Also, the various parts may be replaced by their mechanical equivalents, such as rivets being replaced by threaded fasteners, or the like. Accordingly, the present invention is not limited to the precise embodiments described in detail hereinabove, and shown in the accompanied drawings.

What is claimed is:

1. An ergonomic knee brace comprising:
    an upper strut for extending along the upper leg;
    a lower strut for extending along the lower leg;
    pivoting arrangements for intercoupling said upper strut and said lower strut; said pivoting arrangements having a center; and
    said pivoting arrangements including stop assemblies both for flexion and extension, including:
    a) a catch plate formed of a flat arcuate disc having an arcuate opening and having stop recesses facing or opening toward the center of said pivoting arrangements;
    b) a movable stop pivoted at the center of the assembly and having an outwardly biased locking member for engaging said stop recesses, coupled to a release button which extends radially outward to the periphery of said pivoting arrangements; and
    c) said release button being movable inward to shift said locking member out of said stop recesses to permit angular adjustment of said stop;
    at least one of said struts having a flexion stop surface for engaging the flexion stop assembly; and
    at least one of said struts having an extension stop surface for engaging the extension stop assembly.

2. An ergonomic knee brace assembly comprising a medial knee brace and a lateral knee brace, each as defined in claim 1, padding for mounting between said struts and the patient's leg, and straps for mechanically inter-coupling the upper and lower struts of said medial and said lateral knee braces.

3. A knee brace as defined in claim 1 including two substantially aligned catch plates and wherein said locking member engages both of said catch plates.

4. A knee brace as defined in claim 1 further comprising inner and outer cover plates, and wherein a part of said movable stop extends over said outer cover plate, said outer cover plate having angular indicia thereon.

5. A knee brace as defined in claim 4 wherein said part of said stop member has a window aligned with said indicia whereby said stop may be adjusted to selected angular positions.

6. An ergonomic knee brace comprising:
    an upper strut for extending along the upper leg;
    a lower strut for extending along the lower leg;
    pivoting arrangements for intercoupling said upper strut and said lower strut; said pivoting arrangements having a center; and
    said pivoting arrangements including stop assemblies both for flexion and extension, including:
    a) A generally circular plate, and a generally arcuate array of locking steps;
    b) a movable stop pivoted at the center of the assembly and having an outwardly biased locking member for engaging said locking steps, said locking member being coupled to a release button which extends radially outward to the periphery of said pivoting arrangements; and
    c) said release button being movable inward to shift said locking member out of engagement with said locking steps to permit angular adjustment of said stop,
    at least one of said struts having a flexion stop surface for engaging the flexion stop assembly; and
    at least one of said struts having an extension stop surface for engaging the extension stop assembly.

7. An ergonomic knee brace as defined in claim 6 wherein said knee brace has an outer cover plate having a series of indicia indicating angular positions near the outer edge thereof; and
    wherein said movable stop has a radially extending flat support member overlying said circular plate, and a window opening through which the angular indicia may be seen.

8. A knee brace as defined in claim 6 wherein a matched pair of said arcuate array of locking stops are provided, and wherein said locking member engages a locking stop of each of said array of locking stops, at each angular stop position.

9. A knee brace as defined in claim 8 wherein said knee brace includes an outer cover plate and wherein said stop assembly extends over the outer edge of said outer cover plate.

10. An ergonomic knee brace comprising:
an upper strut for extending extend along the upper leg;
a lower strut for extending along the lower leg;
pivoting arrangements for intercoupling said upper strut and said lower strut; said pivoting arrangements having a center; and
said pivoting arrangements including stop assemblies both for flexion and extension, including:
a) an outer cover plate and an inner cover plate both being fixedly secured to one of said struts;
b) a generally arcuate array of locking steps mounted between said outer and inner cover plates;
c) a movable stop pivoted at the center of the assembly and having an outwardly biased locking member for engaging said locking steps, said locking member being attached to a release button which extends radially outward beyond the periphery of said pivoting assembly;
d) said release button being movable inward to shift said locking member out of engagement with said locking steps to permit angular adjustment of said stop,
said pivoting arrangements being mounted on one of said struts;
the other one of said struts having a flexion stop surface for engaging the flexion stop assembly; and an extension stop surface for engaging the extension stop assembly;
said outer cover plate having a series of indicia indicating angular positions, near the outer edge thereof;
said movable stop assembly having a radially extending flat support member overlying said outer cover plate adjacent the angular indicia; and
said movable stop member extending over the outer edge of the outer cover plate and into the space between said inner and outer cover plates to cooperate with said locking steps;
whereby the configuration of said stop member contributes to the reduced thickness of said pivoting arrangements.

11. A knee brace as defined in claim 10 wherein two sets of locking stops are provided and said locking member engages one locking stop from each of said two sets of locking stops.

12. A knee brace as defined in claim 10 wherein said outer cover plate has angular indicia thereon, and wherein said radially extending flat support member has a window for viewing said angular indicia.

13. An ergonomic knee brace comprising:
an upper strut for extending along the upper leg;
a lower strut for extending along the lower leg;
a pivoting assembly for intercoupling said upper strut and said lower strut; said pivoting assembly having a center; and
said pivoting assembly including stop assemblies both for flexion and extension, including:
a) An outer closure plate and an inner closure plate both being fixedly secured to one of said struts;
b) a generally arcuate array of locking steps mounted between said outer and inner closure plates;
c) a movable stop pivoted at the center of the assembly and having an outwardly biased locking member for engaging said locking steps, said locking member being attached to a release button which extends radially outward beyond the periphery of said pivoting assembly;
d) said release button being movable inward to shift said locking member out of engagement with said locking steps to permit angular adjustment of said stop,
said pivoting assembly being mounted on one of said struts;
the other one of said struts having a flexion stop surface for engaging the flexion stop assembly; and an extension stop surface for engaging the extension stop assembly;
said movable stop having a radially extending flat support member overlying said outer closure plate; and
said movable stop member being cantilevered to extend over the outer edge of said outer closure plate and into the space between said inner and outer closure plates to cooperate with said locking steps;
whereby the cantilevered configuration of said stop member contributes to the reduced thickness of said pivoting arrangements.

14. A knee brace as defined in claim 13 wherein a matched pair of said arcuate array of locking steps are provided, and wherein said locking member engages a locking step of each of said array of locking steps, at each angular stop position.

15. A knee brace as defined in claim 13 wherein angular indicia are provided on said outer closure plate, and wherein said flat support plate overlies said angular indicia to identify the angular position of said stop.

16. An ergonomic knee brace comprising:
an upper strut to extend along the upper leg;
a lower strut for extending along the lower leg;
a pivoting assembly for intercoupling said upper strut and said lower strut; and
said pivoting assembly having at least one stop assembly, including:
a) An outer closure plate and an inner closure plate each being fixedly secured to one of said struts;
b) an array of locking steps within said outer and inner closure plates;
c) a movable stop having an outwardly biased locking member for engaging said locking steps, said locking member being associated with a release button which extends radially outward and is accessible at the periphery of said pivoting assembly; and
d) said release button being movable inward to shift said locking member out of engagement with said locking steps to permit angular adjustment of said stop.

17. A knee brace as defined in claim 16 wherein said movable stop has an outwardly extending flat support member overlying said outer closure plate; and said movable stop member is cantilevered to extend over the outer edge of said outer closure plate and into the space between said inner and outer closure plates to cooperate with said locking steps.

18. A knee brace as defined in claim 16 wherein a matched pair of said array of locking steps are provided, and wherein said locking member engages a locking step of each of said array of locking steps, at each angular stop position.

19. A knee brace as defined in claim 17 wherein angular indicia are provided on said closure plate, and wherein said flat support plate overlies said angular indicia to identify the angular position of said stop.

* * * * *

UNITED STATES PATENT AND TRADEMARK OFFICE
CERTIFICATE OF CORRECTION

| | |
|---|---|
| PATENT NO. | : 7,037,287 B2 |
| APPLICATION NO. | : 10/675324 |
| DATED | : May 2, 2006 |
| INVENTOR(S) | : David Cormier et al. |

Page 1 of 1

It is certified that error appears in the above-identified patent and that said Letters Patent is hereby corrected as shown below:

<u>Title page</u>,
Item 56, FOREIGN PATENT DOCUMENTS, insert --EP 1 086 672   3/2001--.

<u>Column 7</u>,
Line 2, delete "extending extend along" and insert --extending along--.

Signed and Sealed this

Twenty-fourth Day of October, 2006

JON W. DUDAS
*Director of the United States Patent and Trademark Office*